(12) United States Patent
Schultz et al.

(10) Patent No.: US 9,375,142 B2
(45) Date of Patent: Jun. 28, 2016

(54) LEARNING PATIENT MONITORING AND INTERVENTION SYSTEM

(71) Applicants: Christian P Schultz, Beverly, MA (US); Justinian Rosca, West Windsor, NJ (US); Heiko Claussen, Plainsboro, NJ (US); Carolyn Joiner, Dayton, NJ (US); Steven A Russell, Princeton, NJ (US); Nazif Tas, Lawrenceville, NJ (US)

(72) Inventors: Christian P Schultz, Beverly, MA (US); Justinian Rosca, West Windsor, NJ (US); Heiko Claussen, Plainsboro, NJ (US); Carolyn Joiner, Dayton, NJ (US); Steven A Russell, Princeton, NJ (US); Nazif Tas, Lawrenceville, NJ (US)

(73) Assignee: Siemens Aktiengesellschaft, Munich (DE)

( * ) Notice: Subject to any disclaimer, the term of this patent is extended or adjusted under 35 U.S.C. 154(b) by 384 days.

(21) Appl. No.: 13/718,023

(22) Filed: Dec. 18, 2012

(65) Prior Publication Data

US 2013/0245389 A1 Sep. 19, 2013

Related U.S. Application Data

(60) Provisional application No. 61/611,260, filed on Mar. 15, 2012.

(51) Int. Cl.
*A61B 5/00* (2006.01)
*G06F 19/00* (2011.01)
(Continued)

(52) U.S. Cl.
CPC ............... *A61B 5/0002* (2013.01); *A61B 5/68* (2013.01); *G06F 19/345* (2013.01); *G06F 19/3418* (2013.01); *A61B 5/0077* (2013.01); *A61B 5/02* (2013.01); *A61B 5/024* (2013.01); *A61B 5/0205* (2013.01); *A61B 5/0402* (2013.01);
(Continued)

(58) Field of Classification Search
CPC .... A61B 5/0077; A61B 5/0205; A61B 5/024; A61B 5/0402; A61B 5/0813; A61B 5/14542; A61B 5/6892; A61B 5/68; A61B 5/0002; G08B 21/0461; G08B 25/10; G06F 19/345; G06F 19/3418
USPC .................................................. 600/300–301
See application file for complete search history.

(56) References Cited

U.S. PATENT DOCUMENTS 7,225,013 B2 5/2007 Geva et al.
7,285,090 B2 10/2007 Stivoric et al.
(Continued)

OTHER PUBLICATIONS

Shawe-Taylor J., Cristianini N., Kernel Methods for Pattern Analysis, Cambridge University Press, New York, NY, 2004.
(Continued)

*Primary Examiner* — William Thomson
*Assistant Examiner* — Shirley Jian

(57) ABSTRACT

A patient monitoring and intervention system, comprises an interface for receiving data representing multiple different parameters from multiple different sensors, comprising sensors in a patient bed and attached to a patient including, a heart rate sensor, a respiration sensor and a pressure sensor indicating bed pressure points. A learning processor determines a normal range for a set of the different received patient parameters for the patient by recording the patient parameter values over a time period and analyzing the recorded parameter values to determine their range. A data processor determines if the set of different received patient parameters exceeds the determined normal range and in response to this determination and in response to the type of parameters in the set and medical record information of the patient, initiates adjustment of a patient bed and at least one of, (a) changes medication administered to a patient and (b) alerts a worker of the patient parameter change.

20 Claims, 6 Drawing Sheets

(51) Int. Cl.
*A61B 5/02* (2006.01)
*A61B 5/0205* (2006.01)
*A61B 5/024* (2006.01)
*A61B 5/0402* (2006.01)
*A61B 5/08* (2006.01)
*A61B 5/145* (2006.01)
*G08B 21/04* (2006.01)
*G08B 25/10* (2006.01)

(52) U.S. Cl.
CPC .......... *A61B 5/0813* (2013.01); *A61B 5/14542* (2013.01); *A61B 5/6892* (2013.01); *G06F 19/3443* (2013.01); *G08B 21/0461* (2013.01); *G08B 25/10* (2013.01)

(56) References Cited

U.S. PATENT DOCUMENTS

| | | | |
|---|---|---|---|
| 9,005,101 B1* | 4/2015 | Van Erlach | 600/9 |
| 2004/0152957 A1 | 8/2004 | Stivoric et al. | |
| 2004/0230105 A1* | 11/2004 | Geva et al. | 600/301 |
| 2005/0043894 A1 | 2/2005 | Fernandez | |
| 2007/0100666 A1 | 5/2007 | Stivoric et al. | |
| 2007/0157385 A1* | 7/2007 | Lemire et al. | 5/600 |
| 2007/0208232 A1* | 9/2007 | Kovacs | 600/300 |
| 2008/0004904 A1* | 1/2008 | Tran | 705/2 |
| 2008/0171919 A1 | 7/2008 | Stivoric et al. | |
| 2008/0275309 A1 | 11/2008 | Stivoric et al. | |
| 2009/0043216 A1* | 2/2009 | Lin et al. | 600/501 |
| 2009/0099480 A1* | 4/2009 | Salgo et al. | 600/595 |
| 2009/0124870 A1* | 5/2009 | Arends et al. | 600/301 |
| 2009/0248450 A1* | 10/2009 | Fernandez | 705/3 |
| 2010/0231421 A1* | 9/2010 | Rawls-Meehan | 341/20 |
| 2011/0263950 A1* | 10/2011 | Larson et al. | 600/301 |

OTHER PUBLICATIONS

Tipping M. E., Sparse Bayesian learning and the relevance vector machine. Journal of Machine Learning Research 1, pp. 211-244, 2001.

W. Lutz, W. Sanderson, S. Scherbov, 2008 "The coming acceleration of global population ageing", Nature, vol. 451, No. 7179, pp. 716-719.

AASM, 2001 "The International Classification of Sleep Disorders, Revised. Westchester, Illinois: American Academy of Sleep Medicine",. pp. 52-58. http://www.esst.org/adds/ICSD.pdf.

E.R. Frykberg and J.J. Tepaslll "Terrorist Bombings: Lessons Learned from Belfast to Beirut," Annals of Surgery, vol. 208, No. 5, 1988, pp. 569-576.

Lorincz, K.; Malan, D.J.; Fulford-Jones, T.R.F.; Nawoj, A.; Clavel, A.; Shnayder, V.; Mainland, G.; Welsh, M.; Moulton, S.; , "Sensor networks for emergency response: challenges and opportunities," Pervasive Computing, IEEE , vol. 3, No. 4, pp. 16- 23, Oct.-Dec. 2004.

English translation of Office Action in counterpart Chinese application No. 201310083674.8, dated Aug. 27, 2015, 12 pages total.

* cited by examiner

LEARNING PATIENT MONITORING AND INTERVENTION SYSTEM

This is a non-provisional application of provisional application Ser. No. 61/611,260 filed on 15 Mar. 2012, by C. Schultz et al.

FIELD OF THE INVENTION

This invention concerns a patient monitoring and intervention system using sensors in a patient bed and attached to a patient that uses a learning processor for determining a normal range for a set of received patient parameters and in response to parameters exceeding the determined normal range, adjusting a patient bed, changing medication administered to a patient and alerting a worker.

BACKGROUND OF THE INVENTION

It is desirable to enable monitoring and intervention to support patient healthcare in hospitals, homes, other controlled and structured environments as well as in uncontrolled environments such as accident scenes, disaster zones and other outdoor environments. In such settings, there may be a high number of casualties, requiring quick identification and severity categorization. Such a situation is challenging both for monitoring patients and transporting them. A system according to invention principles addresses these needs and associated problems to support seamless concurrent collection of different types of medical data in real-time from a high number of patients as well as supporting automated intervention care for the patients. A system according to invention principles addresses these deficiencies and related problems.

SUMMARY OF THE INVENTION

A system provides a transparent and intelligent hospital patient monitor using a system unit and multiple sensors wired or wirelessly connected to the unit to perform processing, database, and display functions involving generating alarms and performing patient data monitoring, storage and knowledge base functions. A patient monitoring and intervention system, comprises an interface for receiving data representing multiple different parameters from multiple different sensors, comprising sensors in a patient bed and attached to a patient including, a heart rate sensor, a respiration sensor and a pressure sensor indicating bed pressure points. A learning processor determines a normal range for a set of the different received patient parameters for the patient by recording the patient parameter values over a time period and analyzing the recorded parameter values to determine their range. A data processor determines the set of different received patient parameters exceeds the determined normal range and in response to this determination and in response to the type of parameters in the set and medical record information of the patient, initiates adjustment of a patient bed and at least one of, (a) changes medication administered to a patient and (b) alerts a worker of the patient parameter change.

DETAILED DESCRIPTION OF THE INVENTION

Figure 1:
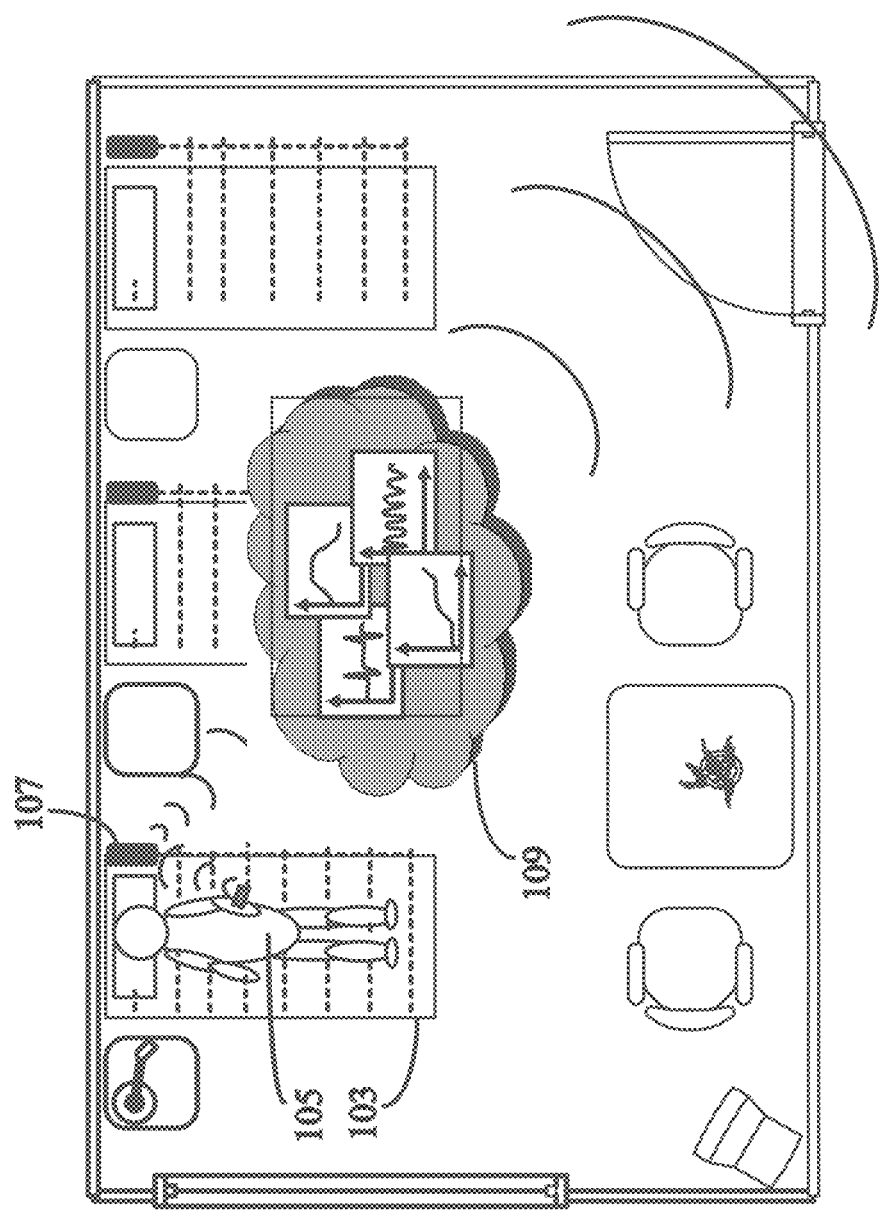
FIG. 1 shows a hospital configuration of sensors incorporated in a patient bed or wirelessly attached to the patient, according to an embodiment of the invention.

FIG. 1 shows a hospital configuration of sensors incorporated in patient bed 103 or wirelessly attached to patient 105 that enables transparent and intelligent hospital patient monitoring. The system in one embodiment incorporates sensors in patient bed 103 and infrastructure where a system unit 107 (also called a sensor bridge) is provided per patient bed. The physical bed has a system-like unit and multiple sensors wired or wirelessly connected to the unit. The beds are connected wirelessly to the infrastructure 109 (e.g. Ethernet) and processing is performed for individual beds on a computer connected to an Ethernet network. System unit 107 takes wired analog inputs and digital inputs from sensors, digitally samples the measurements and routes them to a remote processing station (e.g. a server). The remote server performs processing, database, and display functions generates alarms and performs patient data monitoring, storage and knowledge base functions. The server enables comprehensive secure web server connectivity to patient data by the bed from a nurse station, from a physician location and in a patient home.

Figure 2:
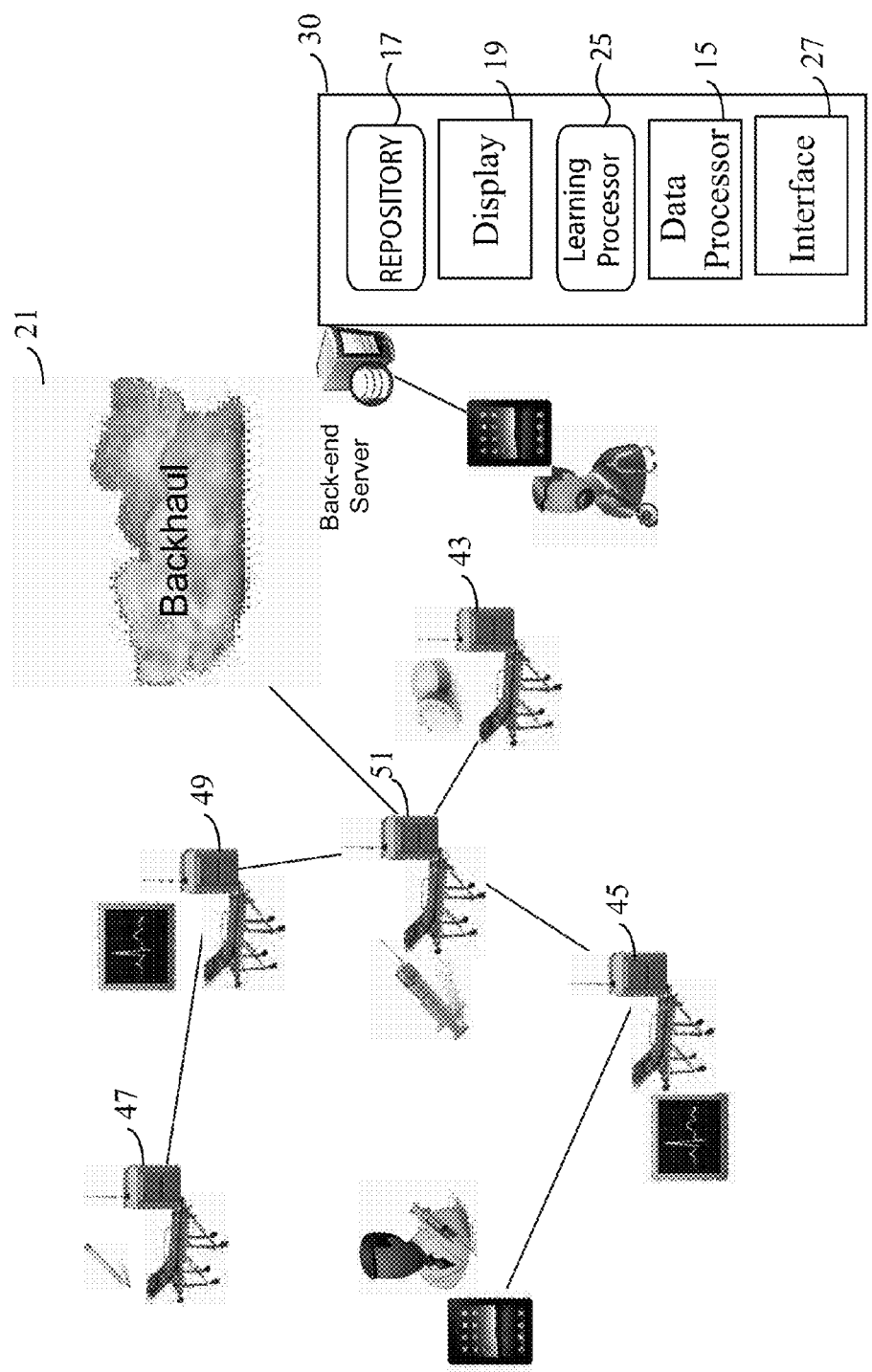
FIG. 2 shows a patient monitoring and intervention system, according to an embodiment of the invention.

FIG. 2 shows patient monitoring and intervention system 10 including a network of monitoring nodes 43, 45, 47, 49 and 51 individually including processing and communication units 107 (FIG. 1) that collaborate together to enable connectivity in a geographically dispersed environment including accident scenes, for example. Physicians and other medical staff communicate with system 10 through an ad hoc network (i.e. a network established for a particular and a potentially temporary function) to a back-end server 30. Server 30 includes data processor 15, learning processor 25, repository 17, interface 27 and display 19. Interface 27 receives data representing multiple different parameters from multiple different sensors, comprising sensors in a patient bed and attached to a patient including, a heart rate sensor, a respiration sensor and a pressure sensor indicating bed pressure points. In one embodiment, server 30 is networked device indicating possible connections to other healthcare resources including patient records and medication information, and connections to other healthcare specialists. Learning processor 25 determines a normal range for a set of the multiple different received patient parameters for the patient by recording the patient parameter values over a time period and analyzing the recorded parameter values to determine their range. Unit 25 also learns norms from sets of data of similar patients and in one embodiment a healthcare worker determines norm parameter. Data processor 15 determines the set of different received patient parameters exceeds the determined normal range and in response to this determination and in response to the type of parameters in the set and medical record information of the patient, processor 15 initiates adjusting a patient bed and at least one of, (a) changing medication administered to a patient and (b) alerting a worker of the patient parameter change.

Repository 17 stores patient sensor parameter value data over a time period, determined patient normal ranges for sets of patient parameters recorded over a time period and data indicating actions and responses performed in response to patient parameter values exceeding determined normal ranges. Display 19 provides messages and alerts to a physician. The autonomous property of the ad hoc network provides local connectivity even in the absence of a broadband connection such as in disaster zones. A unit 107 locally acquires data, preprocesses it and sends necessary information over network 21. Thus, the load on the network and the storage requirements on server 30 are minimized. The definition of necessary sensor information is different for each application and is adaptive or user selectable. Larger data volumes such as raw sensor data may be stored in units 107 locally and can be accessed via high bandwidth connections such as a USB connection, for example.

The ranges of sensors integrated with unit 107 include, wired sensors woven into an intelligent bed or an intelligent room (mattress, pillow, bars, walls). The sensors include, microphones (for breath, heartbeat, gastric sounds), vibration (for pulse, shivering, seizure, muscle cramps and twitching), pressure (for tension, body position, local high-pressure points where tissues may be compressed, determining if a patients leaves a bed), temperature (for fever, blood circulation, comfort), chemical fabric (for urine, sweat, saliva) and specialty pads to be used at certain times (for oximetry, EEG, metabolic, proteomics, genomic expression). Additional portable sensors can be used and connected ad hoc through wireless technology. Thus, the patient is also monitored outside of a bed. For example, sensors in smart devices like tablets and smartphones supply additional data. Additionally, wrist devices measure pulse, temperature, blood pressure, oxygenization, galvanic skin response (GSR) conductivity and provide limited proteomic/genomic chip sampling data. Similar devices are affixed to other extremities or the thorax to enable analysis of the breath or stomach sounds to monitor effects of e.g., diet, gastrointestinal procedures or reactions to drugs. Furthermore, body sensors (including accelerometers) are used to monitor ambulatory signals such as speed (of reaction or movement), stability (e.g., is the patient swaying or stumbling, and flushing), alertness or drowsiness, gait and posture. Cameras (on the bed, eyeglasses or on smart devices) are used for eye tracking, tracking of skin pallor and facial expressions (e.g., indicating pain or fear). Microphones (on the bed, or smart device) are used to evaluate the speech of the patient (e.g., to detect a stroke), body creaks and snaps, sounds of distress or key words (e.g., help or pain). Moreover, smart devices are used for additional input and commands from a patient (e.g., increase temperature, help).

Actuators automatically directed by unit 107 (or worker interaction) control patient bed position (to reduce consequential damage of a heart attack or shock, to prevent breathing and snoring problems) and a medicine dispenser (for avoiding life-threatening conditions). System 10 in one embodiment provides remote homecare monitoring of patients.

Figure 3:
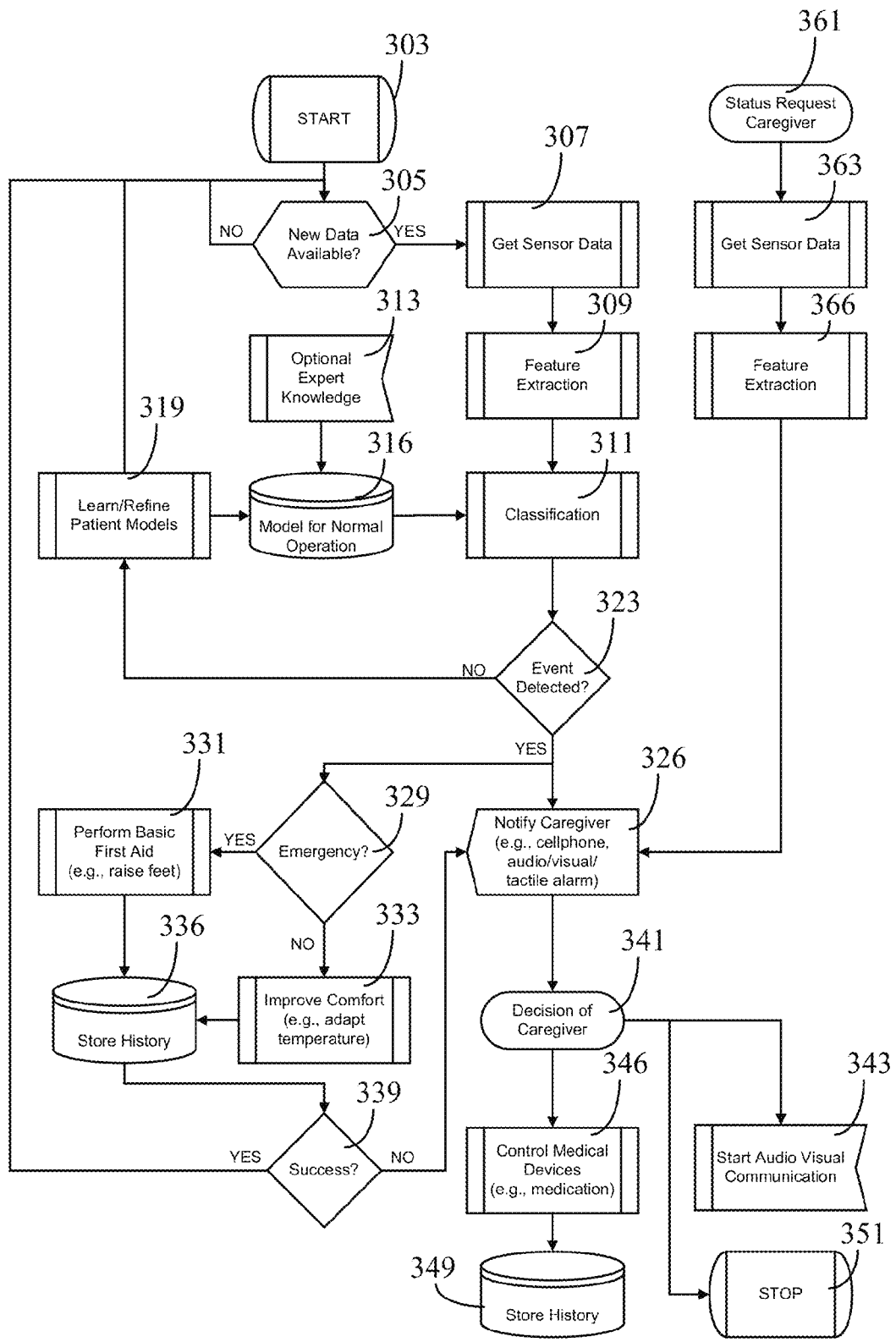
FIG. 3 shows a flowchart of a process for automatic and guided monitoring and intervention for a patient including automatic learning of a patient dependent normal mode of sensor data, according to an embodiment of the invention.

FIG. 3 shows a flowchart of a process for automatic and guided monitoring and intervention for a patient including automatic learning of a patient dependent normal mode of sensor data. Data processor 15 iteratively determines in step 305 whether new sensor data is available following the start at step 303 and if data is available interface 27 acquires the sensor data in step 307 and records the sensor data for later use and archiving. Processor 15 identifies features in the acquired sensor data in step 309 and uses model 316 indicating normal status for the patient in classifying the features as normal or abnormal in step 311. The system also enables physician selection of parameter values for special cases with one patient or a particular set of patients for a given time or set of circumstances. Learning processor 25 in step 319 employs training datasets of data from the patient as well as (optional) expert knowledge 313 in deriving normal patient data model 316. If processor 15 in step 323 identifies features in the acquired sensor data are abnormal and indicate occurrence of an event, a worker is notified of the data in step 326 by audio, visual or tactile alert or communicated message. In response to worker command in step 341 resulting from review of the alert data, medical intervention (e.g. medication administration, use of medical devices) is initiated in step 346 and records of the sensor data, and medical intervention are stored in repository 17 in step 349. In response to worker command in step 341 indicating no intervention is required the process terminates at step 351 and audio-visual communication with the patient and other workers is optionally initiated in step 343.

Processor 15 in step 329 automatically analyzes the event detected in step 323 by comparison of patient parameters or values derived from parameters with thresholds to identify an emergency condition. If an emergency condition is detected, medical intervention actions (e.g. basic first aid, feet raising via bed command, oxygen is delivered) are initiated in step 331 and records of the sensor data, and medical intervention are stored in repository 17 in step 336. Similarly, if no emergency condition is detected in step 329, comfort actions are initiated for the patient in step 333. In response to success of the actions determined in step 339, the process flow is returned to the start and step 305 and the process is repeated. If there is no success detected, process flow proceeds from the notification step 326. Further, in response to a worker status request 361, interface 27 acquires the sensor data in step 363, processor 15 extracts features in the sensor data in step 366 and process flow continues from worker notification step 326.

Learning processor 25 automatically learns patient dependent normal mode sensor data and in one embodiment employs human expert supervision and input into a learning process. Critical decisions of the system and of a supervisor user are recorded and used in a learning mode to aid future treatment. Learning processor 25 acquires live patient data, learns a (normal) patient specific range of different types of parameters across multiple dimensions, monitors for abnormal situations, and controls medical-related devices around a patient in emergency room and homecare environments. The system employs a network of intelligent assistants (units 107) for advanced processing and cloud storage, search, query generation, pattern-based discovery of unusual conditions and trends employing connectivity to health care personnel for telemedicine, remote diagnostics, remote programming, and interactivity. The system transparently (without interaction with nurse or physician) performs functions including acquiring different types of patient data from sensors continuously through unit 107 from a bed and provides the data to data processor 15 via a dynamically configured network to transfer, store and process the data in a distributed manner.

Processor 15 processes the data locally, in the distributed system or remotely and derives inference measurements (by combining sensor data to infer relevant quantities) and performs diagnostic reasoning by learning patient specific normal sensor data specific to a particular patient. Processor 15 also continuously checks sensor functionality to discover bad reading resulting from sensor failure, for example. The system determines patient specific safe limits (minimum, maximum and resting heart rate, for example), performs abnormality detection on live data remotely or at a patient location through comparing the current status of the patient with the patterns learned by processor 25 via sensor data collected from a specific patient under normal conditions and from data derived from a patient population having similar demographics including age, weight, height, gender, pregnancy status as the patient and similar medical conditions. The system also performs abnormality detection using commonly accepted medical and social knowledge and displays measurements and diagnostic data (on web devices and on devices which are authorized to connect to the system network).

System 10 performs other data acquisition and processing functions in a large scale system knowledge base (on a database and one or more processing devices) including storing data in a database, learning from patient data, performing auxiliary functions. System 10 establishes a bridge to acquire information about auxiliary portable equipment connected to a patient and enables audio-visual communication with the patient. The system performs actions e.g., automatically calls a contact person, e.g., if abnormal data is detected, the patient tries to leave the bed or wakes up. The system controls the environment such as temperature, or activates a massage function dependent on sensor data from the patient, controls medicine dispensing and electronic devices such as TV, microwave, turns sleeping patients if breathing problems are detected and performs simple first aid functions such as raising the upper or lower body in a bed. The system also performs actions such as providing inputs to regulatory personnel, legal and facility administration groups and assesses disease spread patterns.

System 10 deploys a robust, efficient mesh communication architecture which enables the system devices to collaboratively maintain the connectivity, even in settings where there is no infrastructure support. For instance, in a disaster zone, the patients can be placed on system-enabled stretchers which collect, analyze and act on data gathered directly from the patients. Each system device further maintains the connectivity to the central system through a mesh topology that is created by the system devices in a collaborative manner. Such a mesh topology further expands wireless range as the devices perform as data collectors and as data forwarders. Hence, each data packet, which is generated from a source system device, chooses the best available route through hopping over several other system devices. Creation, configuration and maintenance operations of the mesh topology are performed automatically and autonomously by the devices themselves without any need of human interaction. Thus, it is not required for the technical staff to be present at the site of deployment.

Figure 4:
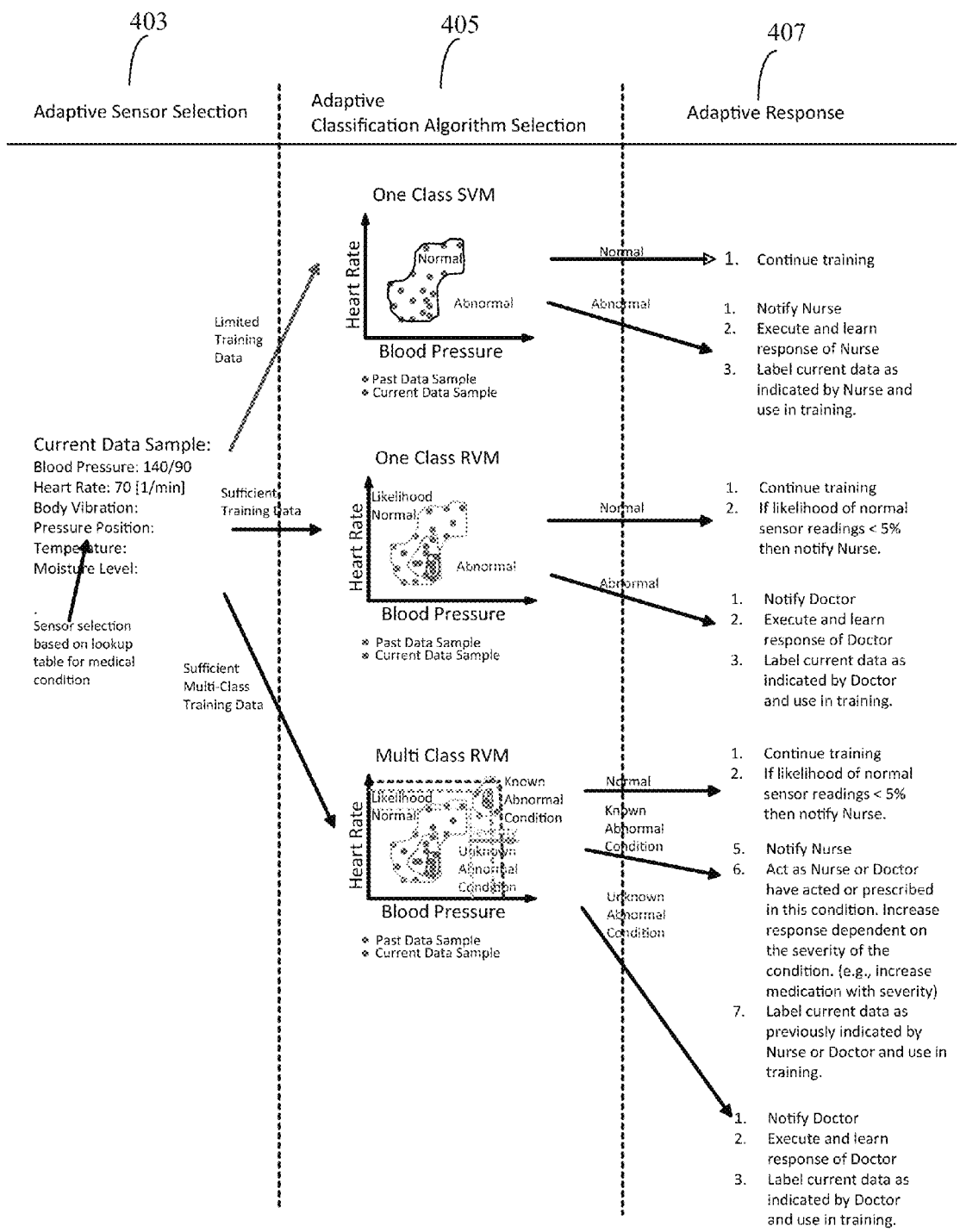
FIG. 4 shows a method of processing acquired sensor data comprising adaptive sensor selection, classification function selection and response or action selection, according to an embodiment of the invention.

FIG. 4 shows a method of processing acquired sensor data comprising adaptive sensor selection, classification function selection and response and action selection. The method has stages that adaptively depend on the medical condition of the patient, the current sensor readings, previous case dependent expert decisions of a Nurse and physician and the amount of available training data. In a first step shown in column 403, data processor 15 (FIG. 2) adaptively selects multiple different sensors from available sensors in response to patient medical condition of the patient and at least one of, (a) current sensor parameter values, (b) decisions of a clinician in a comparable medical case and (c) the amount of available training data, to provide the best treatment in a particular case. A set of sensors is selected such as blood pressure, heart rate, body vibration, pressure at a particular body position and moisture level of a portion of a patient surface, for monitoring that is meaningful for the medical condition of the patient. This adaptive selection in one embodiment is performed using a lookup table configurable by a clinician.

In exemplary operation, for a patient with a heart condition it is important to monitor the blood pressure and the heart rate. The data from the selected sensors is continuously acquired and passed to a training and classification stage performed by learning processor 25 shown in the step of column 405. Learning processor 25 adaptively selects from multiple different functions, a function employed by the learning processor for determining at least one of, (a) a normal range and (b) an abnormal range, for the set of multiple different received patient parameters in response to at least one of, (i) the amount of recorded patient data available from sensors and (ii) the type of recorded patient data available from sensors. The type of recorded patient data comprises types including, normal and healthy patient sensor readings and abnormal patient sensor readings. The multiple functions include at least two of, (a) a one class support vector machine, (b) a one class relevance vector machine and (c) a multiple class relevance vector machine. SVM is described for example in—J. Shawe-Taylor and N. Cristianini. Kernel Methods for Pattern Analysis. Cambridge University Press, New York, N.Y., 2004. (page 211 et seq.). RVM is described for example in—C. M. Bishop. Pattern Recognition and Machine Learning (Information Science and Statistics). Springer, New York, N.Y., 2006. (page 345 et seq.). Processor 25 adaptively selects between different learning machines in response to available information about the patient. For example, a one class kernel support vector machine (One Class SVM) is selected if limited patient data is recorded (determined by comparison with a predetermined threshold) and data from the normal/healthy sensor readings are available.

As follows let $x_i \in R^d$ represent a vector of d sensor readings or features with $i=1, \ldots, N$ comprising one of N training data instances. Furthermore, let $v \in [0,1]$ and $\alpha$ represent the softness of the SVM and the support vector weights. Further, let $K_{ij}=K(x_i,x_j)$ represent an element of the symmetric positive definite kernel matrix K. The cost function of a One Class SVM is given by:

$$W(\alpha) = \alpha^T K \alpha - \alpha^T \text{diag}(K)$$

$$\text{subject to: } \sum_{i=1}^{N} \alpha_i = 1 \text{ and } 0 \le \alpha_i \le \frac{1}{vN}, i=1, \ldots, N$$

Over the set of previously recorded data samples, the weights $\alpha$ are found that minimize this cost function. In the classification step, the One Class SVM assesses if a new data instance is contained in a previously learned hyper-sphere given a threshold $\gamma$, the radius in the kernel space comprises, $$r = \sqrt{K_{ii} - 2\sum_{j=1}^{N} \alpha_j K_{ij} + \sum_{i,j=1}^{N} \alpha_i \alpha_j K_{ij}}$$

and the bias $$D = \sum_{i,j=1}^{N} \alpha_i \alpha_j K_{ij} - r^2 - \gamma$$

is as follows:

$$f(\cdot) = \mathcal{H}\left[K(\cdot,\cdot) - 2\sum_{i=1}^{N} \alpha_i K(x_j, \cdot) + D\right]$$

The boundary of the points that lie inside and outside of this classification is illustrated in the heart rate versus blood pressure plots of column 405. If there is sufficient training data collected to model the likelihood of the feature space then the One Class SVM is replaced by processor 25 by another machine learning method such as the relevance vector machine (RVM). Rather than just returning a normal or abnormal classification, the RVM results in an estimate of the posterior probability of the current state. For example, the output may indicate there is a 95% probability that the sensor data is representing a normal patient condition. If there exists information or data on specific abnormal conditions then these may be trained using a multi-class learning method. Different embodiments employ different sensor selection, learning, and refinement methods and are not restricted to SVM and RVM.

In the step shown in column 407, the results of the classification procedures are used by data processor 15 to adaptively select an action and response. Upon determining the set of multiple different received patient parameters exceeds the determined normal range, the data processor adaptively selects an action to be performed in response to at least one of, (a) the amount of recorded patient data available from sensors, (b) the type of recorded patient data available from sensors, (c) the type of the selected function, (d) a medical condition of the patient and (e) the criticality of the different received patient parameters. For example, as long as learning processor 25 does not have sufficient amounts of data (less than a predetermined threshold amount), the One Class SVM machine learning method is used for classifying patient parameters acquired from a selected set of sensors. In this case confidence in classification is not sufficient to initiate emergency actions when abnormality is detected. Therefore a reduced set of actions is selected and a caregiver or nurse is notified. Data processor 15 initiates the operation as requested by a clinician and records data identifying actions taken. If a pattern is detected and the data allows for modeling, learning processor 25 imitates the recorded behavior of the clinician in a future case. If there exists enough data to give sufficient confidence (e.g., there is a 98% probability) that the patient is showing abnormal behavior and in response to the medical condition of the patient and the criticality of the sensor parameters, data processor 15 notifies the primary physician of the patient. For example, if the patient has a heart condition and the blood pressure rises to an abnormal level immediate action is initiated by processor 15.

In the case of an emergency, a supervisor informs an ambulance and travels to a location while being in contact with a patient. The system also controls the distribution of medication to the patient via a remotely controlled vending machine and reminds the patient automatically to take medication and verify that it is taken. The supervisor provides additional medication, e.g., in emergency situations or if the patient has pain, via a smartphone link to the system. In this way, overdoses are prevented and a physician knows exactly which medication was taken at what point of time in case emergency help is required. The system executes, controls and evaluates physician prescribed training modules for the patient. For example, the system periodically initiates interactive games that include eye movement tracking for stroke recovery or training of muscles and flexibility of joints for rehabilitation. The test results are evaluated and a recovery time is predicted. The patient and physician are informed of progress or need for intervention if recovery is impeded. The system controls household appliances automatically or remotely automatically or in response to supervisor manual interaction. For example, a room temperature is adjusted automatically if the patient is freezing or sweating, a microwave is activated by the supervisor if the patient is hungry. The system is also usable with a smart crib for monitoring the sleep of a child, the child's position (e.g., on the side, stomach or back) and unusual crying patterns to prevent sudden child death, for example.

In another embodiment, the system monitors and improves measured sensor data such as blood pressure, blood oxygen saturation SPO2 and heart rate, of Emergency Room (ER) patients by actively controlling an environment of each bed and accelerating recovery time. For example, temperature in a bed can be automatically controlled dependent on the measured response of the patient, a massage function can be automatically activated to improve blood circulation or other measures can be taken to avoid bed sores or other low-movement problems. Furthermore, the system automatically turns patients during sleep when snoring is detected. This is used to prevent obstructive sleep apnea (OSA). A typical feature of this disorder is hypoxemia that can result in oxygen saturation of less than 50%. Also, cardiac arrhythmias commonly result from OSA. Some OSA patients are predisposed for right-sided cardiac failure, pulmonary hypertension, hepatic congestion, angle edemas and blackouts. Turning is achieved by controlling an air mattress with multiple separately controllable air pockets. The system performs basic first aid such as raising the upper body of a patient if a heart attack or stroke is detected (to lower the pressure on the affected area) or raising the feet of the patient if a cardiovascular system is in shock (to allow a better blood circulation in the head). The immediate administration of such measures minimizes the response time and thus potentially reduces consequential damage until professional aid arrives.

The system monitors people in hazardous environments such as disaster zones (e.g., caused by fire, earthquakes, hurricanes, floods, nuclear failures, terrorist attacks). For example, in case of a large number of victims and damaged infrastructure it is often not possible to help everyone at once. The system monitors the state of different patients and helps to identify the most severely injured patients that require immediate help. Also, the system builds a local communication network and enables real-time access to patient data. This can be used to assess the need for additional help in one region and thus aid the overall emergency response. The system also monitors the status of helpers (e.g., firemen, military personal, physicians, technical personal). For example, tracking positions of helpers enables immediate assistance in case of consequent emergencies (e.g., if a house collapses in a fire burying firemen). Also, information indicating a duration that a person was at a certain location facilitates determination of possible exposure to toxins, contagious infections and radiation. Additionally, sensors attached to helpers are used to map environmental conditions (e.g., temperatures, ambient sounds, radiation, pathogens, flammable gases, CO2 density) and warn others of dangerous areas. The level of stress, exhaustion and exposure to toxic substances is also monitored and used to rotate disaster helpers and equally distribute their physical stress and prevent over exertion and collapse.

The system monitors the sleep of a patient by evaluating heart rate, breathing, pulse and motion of the patient. Each patient is different and is assumed to have a different medical condition. The system continuously adapts and learns normal sensor parameter value output for each patient in predefined physical boundaries, e.g., minimum, maximum heart rate. A supervisor is notified and a local alarm in the bed is activated if the patient wakes up, is fidgeting, tries to leave the bed or shows abnormal sensor data. Abnormal sensor data comprises an irregular or increased heart rate or a slight breathing problem for a patient that has not shown this in the past, for example. In this case, the supervisor activates and accesses a camera in the home of the patient through a smartphone while working with other patients. The supervisor assesses a situation and talks (or communicates via another interaction method such as videoconferencing) with the patient through speakers in the room e.g., to discourage the patient from leaving the bed, to enquire about possible reasons for an abnormal situation or to provide verbal support for the patient.

In an example of operation, John is a 65 year old male who has been living with a heart condition for the last ten years and is monitored by unit 107, which constantly and accurately tracks his heart rhythm and warns him if there is any variation or unusual behavior. The system collects various types of health information from John's body, including temperature, pulse rate and motion data for tracking sudden falls and body hits. John's bed is a smart-bed, with several sensors embedded in the bed structure including chemical sensors which can detect urine, sweating and saliva and also pressure sensors which detect movement and high pressure on body parts. The smart-bed directly communicates with unit 107 and periodically transfers the sensor readings. The unit 107 gathers information from several sources, including the local sensors directly located on unit 107, as well as remote sources such as the sensors embedded on the smart-bed. Unit 107 collates this information and analyzes it in real-time, and estimates a status of the patient. The system continuously learns from patient sensor readings and identifies patient normal parameter readings of the patient through analyzing the historical data gathered from patient sensors. The system accesses common databases and other information resources which provide health data for various types of diseases and health conditions. The system gathers and combines this information with the historical data of the patient and other static data (such as the age, origin and health record of the patient) and discovers the normal readings and sensor readings for the patient. Thus, the system adapts itself to different patients from different backgrounds and age groups, as well as variety of health issues and diseases.

John's smart-bed is also a motorized bed with functionality for adjusting the position of the bed head and foot automatically. Two months ago, John had a major circulatory shock when he was lying on his bed. He could not move and did not have anybody to call for help. Unit 107 immediately identifies the unusual blood pressure, heartbeat and breathing anomalies and alerts emergency medical staff about the condition. Before an ambulance arrives the system utilizes precious minutes by identifying a potential problem by comparing the sensor readings with the signs and symptoms of the common medical emergency issues and detects that John might be going through a circulatory shock. Furthermore, the system is aware that raising the feet higher than the head, commonly known as the Trendelenburg position, is the standard first aid position to mitigate this type of shock; and activates the smart-bed motor to raise the feet and lower the head of the patient. In this case, system intelligently acted as a first aid paramedic to improve patient care.

Figure 5:
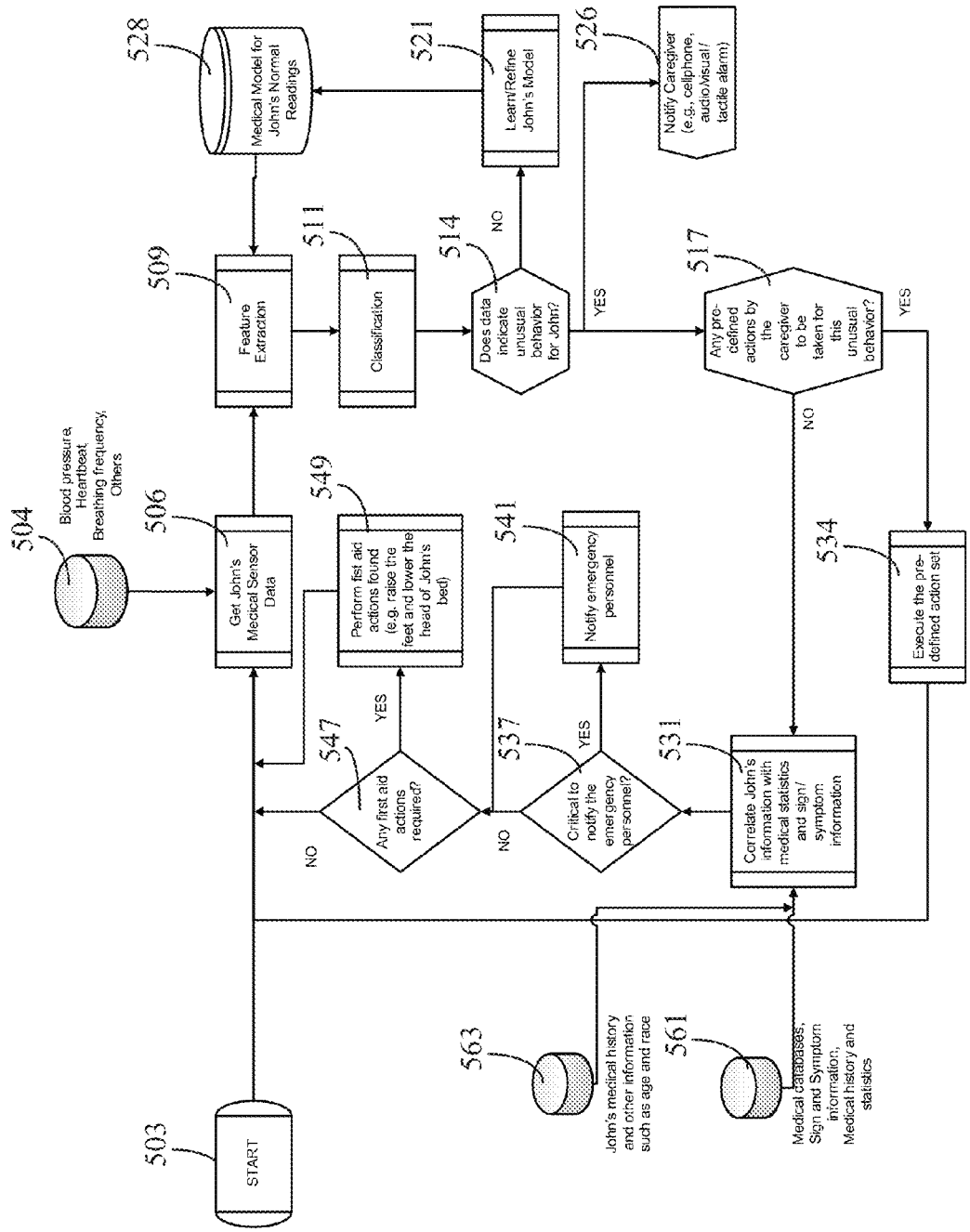
FIG. 5 shows an example flowchart of a home care process for automatically monitoring a patient and identifying an abnormal condition, according to an embodiment of the invention.

FIG. 5 shows an example flowchart of a home care process for automatically monitoring a patient and identifying an abnormal condition of a patient. In step 506, data processor 15 acquires sensor parameter data of a selected set of sensors, from store 504 and extracts data features and patterns in step 509, following the start at step 503. Learning processor 25 classifies the extracted patient data features and patterns in step 511 and determines if the classified data indicates normal or abnormal behavior of the specific patient in step 514. In response to a normal classification, the extracted patient data features and patterns are used to refine the patient model in step 521 and the model is stored in step 528 and the process returns to step 509. Unusual data is excluded from the refinement process in step 521. In some conditions identified based on a combination of sensor readings, the normal values for these readings are themselves dependent on data values from other sensors.

The system identifies sufficiently abnormal sets of values for a given medical condition and in some cases determination of abnormality comprises a sequence of steps rather than just a lookup or single formula. Further, a course of treatment comprises a set of actions and the system re-monitors complex sensor inputs in adapting to particular cases. The system includes capability for detecting sensor differences, by manufacturer, brand, age, position, environment, and sensor data analysis adapts to detected sensor differences. If abnormal behavior is determined in step 514, learning processor 25 alerts a worker in step 526 and data processor 15 determines if a predetermined action is to be taken in response to the abnormal behavior in step 517. If processor 15 determines a predetermined action is to be taken in response to the abnormal behavior, the action is initiated by processor 15 in step 534 and processing returns to step 506. If processor 15 determines no predetermined action is to be taken in response to the abnormal behavior, processor 15 in step 531 correlates patient medical condition data and history (derived from databases 561, 563) with medical symptom and treatment data for a population of patients sharing demographic characteristics with the patient (age, weight, height, gender).

System 10 automatically identifies an abnormal condition of the patient through collating different types of information including medical sensor readings attached to the patient body and bed. Static information such as age and race and common medical information and statistics are gathered from medical databases 563, 561 and information centers. In response to the correlation, processor 15 in step 537 determines whether the patient medical condition is critical and if so notifies a worker in step 541. Processor 15 in step 547 further determines whether first aid intervention is needed and if so initiates the action (e.g. raising feet with respect to head by bed adjustment) in step 549. Processing continues from step 506.

The system derives patient parameters from multiple patient attached and patient room sensors and detects deviations from a recorded complex pattern, determines if deviations are significant and selects an appropriate action from different available actions to perform in response. The system uses advantageous different kinds of sensor data combinations, methods of processing and combining sensor data to provide data patterns for comparison with predetermined patterns of data values and ranges derived from a learning mode identifying a normal pattern for the patient or population of patients. In response to the comparison the system takes actions including moving a patient via actuation of a patient bed component.

The system records patient parameter data continuously indicating patient health status derived from multiple patient attached and patient room sensors and detects deviations from a recorded complex pattern. The system determines if deviations are significant based on a predetermined adaptive threshold and selects an appropriate action from a lookup table associating parameter patterns specific to the patient concerned with actions to be taken including administering medication, adjusting a patient bed and alerting personnel. The system learns from historical patient specific data derived from multiple patient attached and patient room sensors over a time period and diagnoses new data and acts upon it.

The system receives data from sensors, processes the sensor data in combination to derive intermediate results compares the intermediate result with thresholds, ranges, previously recorded data and predetermined patient specific safe (normal) ranges for the patient concerned, to detect complex patterns and to determine if deviations from normal ranges are significant. The system maps a significant result to an action using a lookup table or predetermined rules (the lookup table columns associate sensor data, data derived from combinations of sensor data, associated thresholds, action tasks, data needed to perform specific actions, administer medication, adjust the bed in this specific manner and generates an alert by communication with a destination e.g. via phone, IP address, email). The system learns from monitored data to continuously improve the process Learning processor 25 processes patient data training data sets to learn a model of statistical knowledge comprising complex, multidimensional, patient specific data about the status quo (normality) of a patient across time and space and monitors events that may indicate "abnormal" conditions and require medical decisions to be taken in response. The system changes the environment of the patient by changing the bed temperature, back/footrest position, activation of a massage function, to control parameters that improve the current medical condition or comfort of the patient. The system extracts information on the medical conditions of the patient based on a large number of sensors from multiple modalities worn by the patient or embedded in the environment (bed, room) and detects changes in the medical condition of the patient by jointly utilizing expert knowledge and data-driven abnormality detection using one-class classification, for example. The system includes a user interface that enables interaction between patient and caregiver and intervention of the caregiver in emergencies including but not limited to providing medication. The system employs a network of intelligent assistants (units 107) for advanced processing and cloud storage, search, query, pattern-based discovery of unusual conditions and trends, and connectivity to health care personnel for telemedicine, remote diagnostics, remote programming, and interactivity.

The system deploys a robust, efficient mesh communication architecture which enables the system devices to collaboratively maintain the connectivity in settings where there is no infrastructure support. For instance, in a disaster zone, the patients are placed on system-enabled stretchers which collect, analyze and act on the data gathered directly from the patients. Each system device further maintains connectivity to a central system through the mesh topology that is created by system devices in a collaborative manner. Such a mesh topology further addresses wireless range requirements as the devices perform not only as data collectors but at the same time as data forwarders. Hence, each data packet, which is generated from a source system device, chooses the best available route through hopping through several other system devices. Creation, configuration and maintenance operations of the mesh topology are performed automatically and autonomously by the devices themselves without any need of human interaction.

Figure 6:
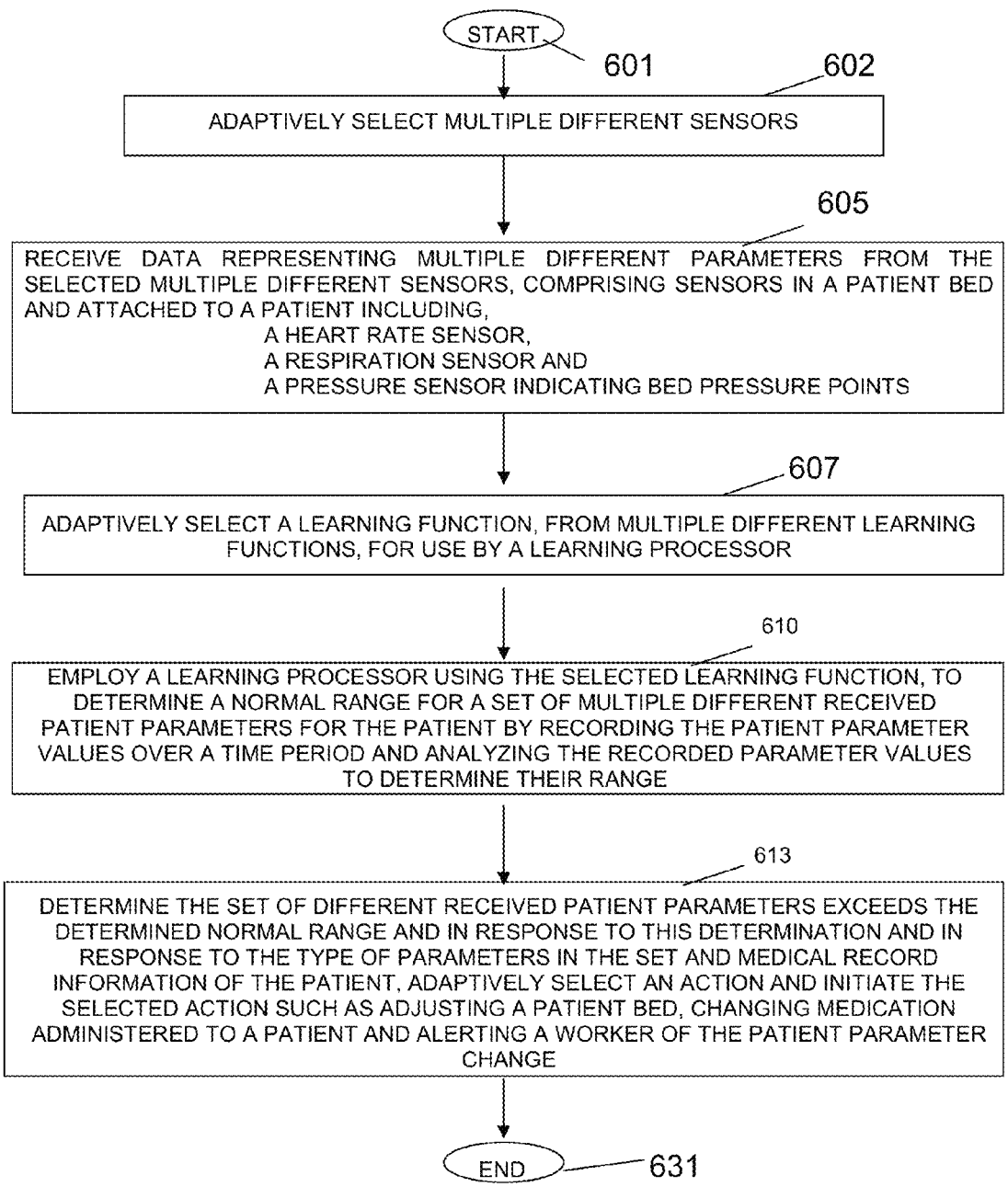
FIG. 6 shows a flowchart of a process performed by a patient monitoring and intervention system, according to an embodiment of the invention.

FIG. 6 shows a flowchart of a process performed by a patient monitoring and intervention system. In step 602 following the start at step 601 data processor 15 adaptively selects multiple different sensors from available sensors in response to patient medical condition of the patient and at least one of, (a) current sensor parameter values, (b) decisions of a clinician in a comparable medical case and (c) the amount of available training data. In one embodiment, data processor 15 selects the set of multiple different received patient parameters from multiple different sets in response to an individual parameter of the multiple different parameters exceeding a predetermined threshold. The sensors include a chemical sensor for sensing a chemical parameter of a body fluid and the set multiple different received patient parameters includes the chemical parameter. The sensors also include a sensor located in at least one of, (a) a mattress, (b) a pillow and (c) a support member of a bed, metabolic system associated sensors and proteomics or genomic expression sensors. The sensors include a microphone for detecting at least one of breath, heartbeat and gastric sounds and the data processor automatically analyzes signal data representing a detected sound to provide a sound parameter and a set of multiple received patient parameters includes the sound parameter. The sensors further include a vibration sensor for detecting at least one of pulse, shivering and seizure and the data processor automatically analyzes signal data representing a detected vibration to provide a parameter derived from vibration and the set of multiple different received patient parameters includes the parameter derived from vibration. The sensors include at least one vital sign sensor for sensing at least one of blood pressure, blood oxygen saturation SPO2, an ECG signal and temperature and the set of multiple different received patient parameters includes a vital sign parameter.

In step 605, interface 27 receives data representing multiple different parameters from multiple different sensors, comprising sensors in a patient bed and attached to a patient including, a heart rate sensor, a respiration sensor and a pressure sensor indicating bed pressure points. The bed pressure points comprise at least one of tension, body position, and local high-pressure points where tissues may be compressed. Learning processor 25 in step 607 adaptively selects from multiple different functions, a function employed by the learning processor for determining at least one of, (a) a normal range and (b) an abnormal range, for the set of multiple different received patient parameters in response to at least one of, (i) the amount of recorded patient data available from sensors and (ii) the type of recorded patient data available from sensors. The normal range is derived from a patient population having similar demographics including age, weight, height, gender, pregnancy status as the patient and similar medical conditions. Training data may come both from the patient (to capture a particular condition) and from other patients (to capture common scenarios, both healthy and abnormal) to facilitate faster multi-class classification and diagnosis. The type of recorded patient data comprises types including, normal and healthy patient sensor readings and abnormal patient sensor readings. The multiple different functions include at least two of, (a) a one class support vector machine, (b) a one class relevance vector machine and (c) a multiple class relevance vector machine. Learning processor 25 learns from cases and supervision and data from new cases is fed in to update the learning. However in a diagnostic mode there is no learning, just the application of the learning and in a production mode, processor 25 in one embodiment comprises a Classifier, Identifier, Diagnoser and Treatment specifier, for example.

In step 610, learning processor 25 determines a normal range for a set of multiple different received patient parameters for the patient by recording the patient parameter values over a time period and using the selected function in analyzing the recorded parameter values to determine their range. Data processor 15 in step 613 determines the set of different received patient parameters exceeds the determined normal range and in response to this determination and in response to the type of parameters in the set and medical record information of the patient and the criticality of the different received patient parameters, adaptively selects an action to be performed. The multiple predetermined actions include, initiating adjusting a patient bed, changing medication administered to a patient, alerting a worker of the patient parameter change, labeling a parameter from a sensor as indicated by a clinician and labeling parameters from sensors for use in training. Action also include automatically turning a patient to support respiration, raising the back or feet. providing medication, reminding the patient and monitoring medication intake and prioritizing treatment in chaotic, understaffed environments such as disaster zones. The process of FIG. 6 terminates at step 631.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system adaptively selects a set of sensor data, a learning processor function to process the selected sensor data to determine a normal patient data range of the sensor data and adaptively selects an action to perform in response to sensor data exceeding the determined normal range. Further, the processes and applications may, in alternative embodiments, be located on one or more (e.g., distributed) processing devices on a network linking the units of FIG. 2. Any of the functions and steps provided in FIGS. 1-6 may be implemented in hardware, software or a combination of both. No claim element herein is to be construed under the provisions of 35 U.S.C. 112, sixth paragraph, unless the element is expressly recited using the phrase "means for."

What is claimed is:

1. A patient monitoring and intervention system, comprising:
    an interface for receiving data representing a plurality of different parameters from a plurality of different sensors, comprising sensors in a patient bed and configured to be attached to a patient including,
        a heart rate sensor,
        a respiration sensor and
        a pressure sensor indicating bed pressure points;
    a learning processor for determining a normal range for a set of a plurality of said different received patient parameters for said patient by recording the patient parameter values over a time period and analyzing the recorded parameter values to determine their range;
    a data processor in communication with a first database and a second database, said processor for selecting, based on a configurable lookup table of medical conditions, said plurality of different sensors from predetermined available sensors in response to at least patient medical condition data of the patient derived from a first database, and for determining the set of different received patient parameters that exceeds the determined normal range;
    one or more actuators in communication with the data processor and connected to the patient bed, wherein the data processor for adjusting, via the one or more actuators, the patient bed in response to this determination and in response to type of parameters in the set and medical record information of said patient;

said data processor for selecting said plurality of different sensors further in response to at least one of,
(a) decisions of a clinician in a comparable medical case stored in the second database, and
(b) the amount of available data stored in the second database; and a display in communication with the data processor for alerting a worker of the a patient parameter change.

2. A system according to claim 1, wherein
said data processor for selecting said set of said plurality of said different received patient parameters from a plurality of different sets in response to an individual parameter of said set exceeding a predetermined threshold.

3. A system according to claim 1, wherein
said sensors include a chemical sensor for sensing a chemical parameter of a body fluid and said set of a plurality of said different received patient parameters includes said chemical parameter.

4. A system according to claim 1, wherein
said sensors include a sensor located in at least one of, (a) a mattress, (b) a pillow and (c) a support member of a bed.

5. A system according to claim 1, wherein
said sensors include a microphone for detecting at least one of breath, heartbeat and gastric sounds or vibrations and said data processor automatically analyzes signal data representing a detected sound to provide a sound parameter and said set of a plurality of said different received patient parameters includes said sound parameter.

6. A system according to claim 1, wherein
said sensors include at least one of, (a) a vibration sensor and (b) a camera for detecting at least one of pulse, shivering and seizure and said data processor automatically analyzes signal data representing a detected vibration to provide a parameter derived from vibration and said set of a plurality of said different received patient parameters includes said parameter derived from vibration.

7. A system according to claim 1, wherein
said sensors include at least one vital sign sensor for sensing at least one of blood pressure, blood oxygen saturation SPO2, an ECG signal and temperature and said set of a plurality of said different received patient parameters includes a vital sign parameter.

8. A system according to claim 1, wherein
said pressure sensor for indicating said bed pressure points including at least one of tension, body position, and local high-pressure points where tissues may be compressed.

9. A system according to claim 1, wherein
said data processor for automatically initiating automatic prioritizing treatment, in response to said determination of the set of different received patient parameters exceeding the determined normal range.

10. A system according to claim 1, wherein
said sensors include proteomics or genomic expression sensors.

11. A system according to claim 1, further comprising a third database in communication with the data processor, wherein the third database stores data from a patient population having similar demographics including age, weight, height, gender, pregnancy status as the patient and similar medical conditions, wherein the data processor derives said normal range from the data.

12. A system according to claim 1, further comprising a third database in communication with the learning processor, wherein the third database for storing training data, wherein said learning processor for adaptively selecting, based on amount of the training data available, from a plurality of different predetermined functions, a function employed by said learning processor for determining at least one of, (a) a normal range and (b) an abnormal range, for said set of a plurality of said different received patient parameters in response to at least one of, (i) the amount of recorded patient data available from sensors and (ii) the type of recorded patient data available from sensors.

13. A system according to claim 12, wherein
said plurality of different functions include at least two of, (a) a one class support vector machine, (b) a one class relevance vector machine and (c) a multiple class relevance vector machine.

14. A system according to claim 12, wherein
said data processor, in response to determining said set of said plurality of said different received patient parameters exceeds the determined normal range, for adaptively selecting an action to be performed, wherein said selection is made in response to at least one of, (a) the amount of recorded patient data available from sensors, (b) the type of recorded patient data available from sensors and (c) the type of the selected function.

15. A system according to claim 12, wherein
said data processor, in response to determining said set of said plurality of said different received patient parameters exceeds the determined normal range, for adaptively selecting from a plurality of predetermined actions, an action to be performed, wherein said selection is made in response to at least one of, (a) a medical condition of the patient and (b) the criticality of said different received patient parameters.

16. A system according to claim 15, wherein
said plurality of predetermined actions include, initiating adjusting a patient bed, changing medication administered to a patient, alerting a worker of the patient parameter change, labeling a parameter from a sensor as indicated by a clinician and labeling parameters from sensors for use in training.

17. A system according to claim 1, including
a mesh communication network deployed by said system, said network for enabling said devices in said system to collaboratively maintain connectivity, wherein said devices include said sensors.

18. A patient monitoring and intervention system, comprising:
an interface for receiving data representing a plurality of different parameters from a plurality of different sensors, comprising sensors in a patient bed and configured to be attached to a patient;
a learning processor for determining a normal range for a set of a plurality of said different received patient parameters for said patient by recording the patient parameter values over a time period and analyzing the recorded parameter values to determine their range;
a data processor for selecting, based on a configurable lookup table of medical conditions, said plurality of different sensors from predetermined available sensors in response to at least patient medical condition data of the patient derived from a first database, and in response to determining said set of said plurality of said different received patient parameters exceeds the determined normal range, for adaptively selecting an action to be performed from a plurality of different predetermined actions in response to at least one of, (a) a medical condition of the patient and
(b) the criticality of said different received patient parameters,
said actions comprising at least one of,
   (i) initiating, via one or more actuators in communication with the data processor, adjusting a patient bed, and
   (ii) changing, via a medicine dispenser in communication with the data processor, medication administered to the patient; and
a second database in communication with the data processor, wherein said data processor selects said plurality of different sensors further in response to at least one of,
   (a) decisions of a clinician in a comparable medical case stored in the second database, and
   (b) the amount of available data stored in the second database;
a display in communication with the data processor for alerting a worker of the patient parameter change.

19. A patient monitoring and intervention system, comprising:
an interface for receiving data representing a plurality of different parameters from a plurality of different sensors, comprising sensors in a patient bed and configured to be attached to a patient;
a learning processor for,
   adaptively selecting, based on amount of training data available, from a plurality of different predetermined functions, a function for determining at least one of, (a) a normal range and (b) an abnormal range, for said set of a plurality of said different received patient parameters, in response to at least one of, (i) the amount of recorded patient data and (ii) the type of recorded patient data, available from said plurality of different sensors and
   determining a normal range or a degree of abnormality for said set of said plurality of said different received patient parameters for said patient by recording the patient parameter values over a time period and using the selected function in analyzing the recorded parameter values to determine their range;
a data processor, in response to determining said set of said plurality of said different received patient parameters exceeds the determined normal range, for adaptively selecting an action from multiple different predetermined actions to be performed in response to at least one of, (a) the amount of recorded patient data available from sensors, (b) the type of recorded patient data available from sensors and (c) the type of the selected function; and
a display in communication with the data processor for alerting a worker of the patient parameter change.

20. A method for patient monitoring and intervention, comprising the activities of:
receiving, via an interface, data representing a plurality of different parameters from a plurality of different sensors, comprising sensors in a patient bed and configured to be attached to a patient including,
   a heart rate sensor,
   a respiration sensor and
   a pressure sensor indicating bed pressure points;
determining, by a learning processor, a normal range for a set of a plurality of said different received patient parameters for said patient by recording the patient parameter values over a time period and analyzing the recorded parameter values to determine their range;
selecting, by a data processor, based on a configurable lookup table of medical conditions, said plurality of different sensors from predetermined available sensors in response to patient medical condition data of the patient and at least one of,
   (a) decisions of a clinician in a comparable medical case stored in the second database, and
   (b) the amount of available data stored in the second database;
determining, by the data processor, said set of different received patient parameters exceeds the determined normal range and in response to this determination and type of parameters in the set and medical record information of said patient, initiating adjusting a patient bed; and
communicating, by a communication device, a message to alert a worker of the patient parameter change.

* * * * *